United States Patent [19]

Mergens et al.

[11] Patent Number: 5,397,576
[45] Date of Patent: Mar. 14, 1995

[54] SPRAY TRITURATED MICRONUTRIENT COMPOSITIONS

[75] Inventors: William J. Mergens, West Caldwell; Joseph E. Raymond, Hasbrouck Heights, both of N.J.

[73] Assignee: Hoffmann-La Roche Inc., Nutley, N.J.

[21] Appl. No.: 62,685

[22] Filed: May 14, 1993

Related U.S. Application Data

[63] Continuation of Ser. No. 950,381, Sep. 23, 1992, abandoned.

[51] Int. Cl.⁶ .................. A61K 9/16; A61K 31/70; A61K 31/495; A61K 31/415
[52] U.S. Cl. .................. 424/493; 424/499; 514/52; 514/249; 514/392
[58] Field of Search .......... 514/52, 951, 952, 251, 514/249, 392, 774, 777, 778, 781; 424/493, 499

[56] References Cited

U.S. PATENT DOCUMENTS

| | | | |
|---|---|---|---|
| 3,175,948 | 3/1965 | Koff et al. | 514/474 |
| 3,293,132 | 12/1966 | Stoyle et al. | 514/474 |
| 3,396,226 | 8/1968 | Cavalli et al. | 514/474 |
| 3,914,430 | 10/1975 | Cannalonga et al. | 514/458 |
| 4,486,435 | 12/1984 | Schmidt et al. | 514/52 |
| 4,489,026 | 12/1984 | Yalkowsky | 264/123 |
| 4,533,674 | 8/1985 | Schmidt et al. | 514/474 |
| 4,830,859 | 5/1989 | Finnan et al. | 424/489 |
| 4,994,458 | 2/1991 | Killbridge, Jr. | 514/251 |
| 5,000,888 | 3/1991 | Killbridge, Jr. et al. | 514/251 |

FOREIGN PATENT DOCUMENTS

| | | |
|---|---|---|
| 363733 | 4/1990 | European Pat. Off. |
| 416773 | 8/1990 | European Pat. Off. |
| 85/01877 | 5/1985 | WIPO |

OTHER PUBLICATIONS

Handbook of Pharmaceutical Excipients (1986) Published by the American Pharmaceutical Assn et al. pp. 39 and 40.

*Primary Examiner*—Raymond Henley, III
*Attorney, Agent, or Firm*—George M. Gould; George W. Johnston; John P. Parise

[57] ABSTRACT

Substantially dried free flowing micronutrient compositions having up to 15% by weight of a micronutrient, a binder, and a densifying agent are produced according to the invention. The process for producing the compositions includes the steps of dissolving or dispersing up to approximately 15% by weight of the micronutrient and a binding amount of a binder in water to obtain an aqueous mixture; suspending a densifying amount of a solid densifying agent in the mixture, the densifying agent having a particle size of approximately 40 mesh to approximately 325 mesh; and spray drying the suspension to produce the micronutrient composition.

14 Claims, No Drawings

SPRAY TRITURATED MICRONUTRIENT COMPOSITIONS

This is a continuation of application Ser. No. 07/950,381, filed Sept. 23, 1992, now abandoned.

FIELD OF THE INVENTION

The invention relates to micronutrient compositions and to methods of preparing micronutrient compositions. In particular, the invention relates to free-flowing, micronutrient compositions and to spray drying methods for producing the compositions.

BACKGROUND OF THE INVENTION

Within the class of vitamins, several have recommended daily allowances (RDA) in the area of micrograms per day and are defined as micronutrients. Examples of some micronutrients are Vitamin B12 which has an RDA of 1.5 to 12.0 μg/day; folic acid has an RDA of 100 to 800 μg/day; and biotin which has an RDA of 75 to 300 μg/day. The proper distribution of these micronutrients in tablets or other vehicles of administration like foods is a difficult task unless special steps are taken to reduce the crystal size and serially dilute the active substance prior to or during the manufacture of the end product.

U.S. Pat. No. 5,000,888 to Killbride et al. discloses spray-drying a riboflavin slurry. The slurry is comprised of 10–50 parts riboflavin, 0.5–15 parts of a binder, and 50–75 parts of water, such that the mixture contains 40–75 weight % water. In an example, the process yielded a final composition containing 94 weight % riboflavin, 5 weight % binder, and 1 weight % water.

Kilbride (U.S. Pat. No. 4,994,458) teaches a riboflavin composition made via a rotary fluidized bed granulator. The product of the process comprises about 70–99.5 weight % riboflavin, and 0.5–25 weight % binder.

Schmidt et al. (U.S. Pat. No. 4,533,674) teach a process for preparing a powder containing 90 weight % ascorbic acid, less than 9 weight % binder, 0.2–2 weight % silicon dioxide, and 0.2–5 weight % lubricant. Densifying agents are not included in the compositions.

Ono, et al., (EP 416,773) describe a vitamin B12 composition dispersed in a mixture of starch and dextrin. The dextrin and starch are mixed together, and an aqueous solution of vitamin B12 is added to form a slurry, which then is spray dried to form the composition. The vitamin B12 is present in the dried composition at about 0.5–1.0 weight %, and the dextrin is present at about 5–30 weight % based on the total weight of B12, dextrin and starch in the composition.

Cannalonga et al. (U.S. Pat. No. 3,914,430) teach a spray drying technique for preparing agglomerated powders. The technique involves the introduction of an absorbent material, e.g., dicalcium phosphate, into the spray drying chamber with an emulsion of water, vitamin and hydrolyzed gelatin. The absorbent particles are coated onto the emulsion ingredients to form the agglomerates. Examples of resulting products therefrom include vitamin E encapsulated in hydrolyzed gelatin, vitamin A encapsulated in hydrolyzed gelatin, vitamin A encapsulated in gum acacia, vitamin D encapsulated in hydrolyzed gelatin, and riboflavin encapsulated in maltrin. The resulting powders have 40–60 weight % vitamin, 1–5 weight % absorbent, and 35–59 weight % gelatin.

Cavalli et al. (U.S. Pat. No. 3,396,226) teach dry-mixed compositions containing up to about 80 weight % ascorbic acid, up to about 50 weight % microcrystalline cellulose, and from 0.07–5.0 weight % of a lubricant, e.g., calcium stearate.

Stoyle et al. (U.S. Pat. No. 3,293,132) disclose compositions containing 75–95 weight % ascorbic acid, 5–25 weight % carbohydrate, e.g., sugars or starches, and 0.5–7 weight % binder, e.g., gelatins. The compositions are prepared by dissolving the carbohydrate and binder in water, adding the ascorbic acid to form a slurry having 40–60 weight % solids, spray-drying the slurry, and then adding a lubricant to form the product.

Schmidt et al. (WO 85/01877) teach compositions containing at least 80 weight % of a water-soluble vitamin, less than 15 weight % of a binder, e.g., gelatins; 0.2–2 weight % adsorbent, e.g., silicon dioxide; 0.2–5 weight % lubricant, e.g., stearic acid; and less than 3 weight % of other excipients, e.g., sugars, starch, etc. The compositions are prepared by spray-drying an aqueous slurry of a water-soluble vitamin and a binder, in the presence of a lubricant and adsorbent.

SUMMARY OF THE INVENTION

The invention is directed to micronutrient compositions and to methods of producing same. In particular, the invention concerns substantially dried micronutrient compositions comprising up to approximately 15% by weight of a micronutrient, a binding amount of a binder, a densifying amount of a densifying agent, and silicon dioxide. The substantially dried compositions typically have a density of about 0.8 g/cc to about 1.1 g/cc.

The invention also is directed to a liquid suspension comprising at least 35% by weight of water; and up to 65% by weight solids. The solids therein including up to 15% by weight of a micronutrient, approximately 7–10% by weight of a binder, about 75%–92% by weight of a insoluble densifying agent, and about 0.4–3% by weight of silicon dioxide.

The method of producing the micronutrient compositions according to the invention comprises the steps of dissolving or dispersing up to approximately 15% by weight of the total final solid content of the micronutrient and a binding amount of a binder in water to obtain an aqueous solution or suspension. A densifying amount of a solid densifying agent then is suspended in the solution. Typically the densifying agent has a particle size of approximately 40 mesh to approximately 325 mesh. The suspension then is spray dried to produce the micronutrient composition.

The substantially dried compositions of the invention have direct blendability, excellent flow properties, high densities, and excellent color and chemical stability, making them very suitable for use as additives for foodstuffs and in tablets.

DETAILED DESCRIPTION OF THE INVENTION

The invention concerns substantially dried micronutrient compositions comprising up to approximately 15% by weight of a micronutrient, a binding amount of a binder, a densifying amount of a densifying agent, and silicon dioxide. The composition typically has a density of about 0.8 g/cc to about 1.1 g/cc.

What is meant by "substantially dried micronutrient composition" is composition of the invention having a moisture content of about 1 weight percent to about 5 weight percent.

Typical micronutrients suitable for the invention are vitamin B-12, folic acid, biotin and the like. The micronutrients are present in the final composition in amounts of up to 15% by weight of the total composition. Preferably, the biotin and B12 are present at about 0.5% to about 5% by weight of the total composition, most preferably in amounts of about 1% by weight. For folic acid, the range of about 5-15 weight %, and preferred is about 10 weight %.

Species of vitamin B-12 suitable for the invention include cyanocobalamin, cyanocobalamin hydrate.

The compositions of the invention contain a binder which is generally present in an amount of about 10% by weight of the total composition. Suitable binders include, for example, those materials which are usually polymeric in nature that exhibit cohesive properties and are capable of adhering the active material to the densifier, and in addition, can protect the active material (micronutrient) from chemical hydrolysis, oxidation, etc. deterioration. Preferred binders are maltodextrins, gelatins, starches, and celluloses, with maltodextrins being the most preferred binder. Preferably the binder is present in an amount of approximately 7% to 8% by weight.

The compositions of the invention also contain a densifying agent in an amount of approximately 75% to 92% by weight of the total substantially dried composition. Typical densifying agents include, for example, alkaline earth sulfates, alkali carbonates and alkaline earth phosphates. Preferred densifying agents are calcium sulfate, barium sulfate and di-calcium phosphate dihydrate.

The compositions of the invention typically have tapped densities of about 0.7 g/cc to about 1.2 g/cc. Preferably, the tapped density of the composition is from about 0.8 g/cc to about 1.1 g/cc.

Another aspect of the invention is a liquid suspension comprising at least 35% by weight of water; and up to 65% by weight solids. The solids therein including up to 15% by weight of total solids of a dissolved or dispersed micronutrient, approximately 7-10% of a binder, and about 75%-90% by weight of a insoluble densifying agent. Typically, the suspensions have a density of about 1.4 g/cc to about 1.6 g/cc. For example, the suspensions of the invention, at room temperature (23° C.) and 65% solids, have densities of approximately 1.57 g/mL (1% biotin), 1.57 g/mL (1% cyanocabalomin), and 1.44 g/mL (10% folic acid). In contrast, conventional spray-dry feed-solutions have densities in the range of 0.98 to about 1.2 g/mL. See, for example, Table I:

TABLE I

| Product Description | Density of Feed Solution (gms/ml) | Temp °C. |
|---|---|---|
| Dry Vitamin E 50% - Emulsion (oil + H₂O/gelatin) | 1.047-1.050 | 55-60 |
| Rocoat Thiamine Mononitrate 33⅓% - Suspension in Wax | 1.010 | 75 |
| Rocoat Riboflavin 33⅓% - Suspension in Wax | 1.075 | 75 |
| Rocoat Pyridoxine HCl 33⅓% - Suspension in Wax | 1.000 | 75 |
| Rocoat Niacinamide 33⅓% - Suspension in Wax | 0.980 | 75 |
| Vitamin D₃ 2000 SD - Emulsion | 1.102 | 60 |

TABLE I-continued

| Product Description | Density of Feed Solution (gms/ml) | Temp °C. |
|---|---|---|
| Sodium Sulfadimethoxine - Solution | 1.190-1.200 | 25 |

Another aspect of the invention concerns the process used in preparing the micronutrient compositions. The micronutrient compositions of the invention can be produced by dissolving or dispersing up to approximately 15% by weight of the micronutrient and a binding amount of a binder in water to obtain an aqueous solution or suspension. A densifying amount of a solid densifying agent then can be suspended in the micronutrient-binder solution. The suspension then can be spray-dried to form the micronutrient composition.

Preferably, the inlet temperature of the spray-dryer is between 180° C. and 200° C., and the outlet temperature is between 85° C. and 110° C., with the overall change in temperature between inlet and outlet being approximately 70° C. to 115° C. Since the process of spray-drying is well known in the art, the specific spray-drying process conditions needed for the invention are not critical and thus can be determined by one having skill in the art.

Preferably, the binder is present in an amount of approximately 7% to 8% by weight of total solids. The densifying agent is present in an amount of approximately 80% to 90% by weight of total solids.

In a preferred embodiment, approximately 1% by weight of vitamin B-12 and approximately 10% by weight of maltodextrin are dissolved in water to form an aqueous solution. Approximately 89% by weight of calcium sulfate then is suspended in the solution, and the suspension then is spray dried simultaneously with 0.5-1.5 weight percent silicon dioxide.

The following examples are provided to further illustrate the invention and are not to be construed as a limit on the scope of the invention, which scope is defined by the appended claims. Unless otherwise indicated, the examples were carried out as written.

EXAMPLES

In general, the procedure for preparing the compositions of the invention entails charging a suitable vessel with the formulation amount of distilled or deionized water at approximately 45-60° C. With continuous agitation, the formulation amount of binder is added and mixed until dissolved. The micronutrient then is added to the solution and mixed until completely solubilized or dispersed. To the solution is added the formulation amount of the insoluble densifying agent and the slurry is mixed until homogeneous flow properties are obtained. The slurry then can be spray dried according to conventional methods.

EXAMPLE 1

1% Vitamin B-12 Formulation

In a 6 liter vessel, 1500 mL of water was heated to approximately 70° C. To the water is added 200 grams of Maltrin MD 040 (maltodextrin) with continuous mixing until dissolved. Then 25.0 grams of Vitamin B-12 hydrate (88.1%, B12) was added to the solution and the solution mixed until the vitamin was dissolved. With continuous mixing, calcium sulfate (1775 grams) was slowly added to the vitamin solution until a uniform suspension resulted. The suspension then was gravity fed into a a Niro 40 Utility spray dryer having an inlet temperature of 185° C., an outlet temperature of 100° C., a wheel speed of 15,000 rpm, with 1.5 weight percent silicon dioxide (Syloid 74) being simultaneously fed into the dryer.

The tapped density of the substantially dried composition was 0.88 g/100 mL (54.9 lb./ft$^3$).

EXAMPLE 2

10% Folic Acid Formulation

In a 6 liter vessel, 1000 mL of water was heated to approximately 60° C. To the water is added 200 grams of Malttin MD 040 (maltodextrin) with continuous mixing until dissolved. Then 240 grams of Folic acid (92%) was added to the solution and the solution mixed until the folic acid was dissolved. With continuous mixing, calcium sulfate (1560 grams) was slowly added, along with an additional 1000 mL of water, to the folic acid solution until a uniform suspension resulted. The suspension then was gravity fed into a a Niro 40 Utility spray dryer having an inlet temperature of 180° C., an outlet temperature of 90° C.–100° C., a wheel speed of 20,000 rpm, with 1.5 weight percent silicon dioxide (Syloid 74) being simultaneously fed into the dryer.

The tapped density of the substantially dried composition was 0.89 g/100 mL (55.6 lb./ft$^3$).

EXAMPLE 3

1% Biotin Formulation

In a 6 liter vessel, 1500 mL of water was heated to approximately 70° C. To the water is added 200 grams of Maltrin MD 404 (maltodextrin) with continuous mixing until dissolved. Then 22.0 grams of Biotin USP, Food Chemicals Codex, (FCC), was added to the solution and the solution mixed until the biotin dispersed. With continuous mixing, calcium sulfate (1778 grams) was slowly added to the biotin solution until a uniform suspension resulted. The suspension then was gravity fed into a a Niro 40 Utility spray dryer having an inlet temperature of 190° C.–200° C., an outlet temperature of 100° C.–110° C., a wheel speed of 15,000 rpm, with 1.5 weight percent silicon dioxide (Syloid 74) being simultaneously fed into the dryer.

The loose bulk density of the substantially dried composition was 86.5 g/100 mL (54 lb./ft$^3$); and the tapped density was 103.0 g/100 mL (64.3 lb./ft$^3$).

EXAMPLE 4

1% Biotin Formulation

In a 6 liter vessel, 1500 mL of water was heated to approximately 70° C. To the water is added 200 grams of Malttin MD 404 (maltodextrin) with continuous mixing until dissolved. Then 22.0 grams of Biotin USP, Food Chemical Codex was added to the solution and the solution mixed until the biotin dispersed. With continuous mixing, di-calcium phosphate dihydrate (1778 grams) was slowly added to the biotin solution until a uniform suspension resulted. The suspension then was gravity fed into a a Niro 40 Utility spray dryer having an inlet temperature of 190° C.–200° C., an outlet temperature of 100° C.–110° C., a wheel speed of 15,000 rpm, with 1.5 weight percent silicon dioxide (Syloid 74) being simultaneously fed into the dryer.

The loose bulk density of the substantially dried composition was 76.6 g/100 mL (47.8 lb./ft$^3$); and the tapped density was 87.9 g/100 mL (54.9 lb./ft$^3$).

What is claimed is:

1. A process for producing a substantially dried micronutrient composition, comprising the steps of:
    (a) dissolving or dispersing up to approximately 15% by weight of the micronutrient and from approximately 7% to approximately 10% by weight of a binder selected from the group consisting of maltodextrin and gelatin in water to obtain an aqueous mixture;
    (b) suspending approximately 75% to approximately 92% by weight of an insoluble solid densifying agent having a particle size ranging from approximately 40 mesh to approximately 325 mesh in the aqueous mixture to form a suspension; and
    (c) spray drying the suspension to produce the micronutrient composition, whereby in the composition the micronutrient and the binder are adhered around individual particles of the insoluble solid densifying agent in such a manner that the particle size of the insoluble solid densifying agent determines the particle size of the micronutrient composition.

2. The process according to claim 1, wherein the micronutrient is vitamin B-12.

3. The process according to claim 1, wherein the micronutrient is folic acid.

4. The process according to claim 1, wherein the micronutrient is biotin.

5. The process according to claim 1, wherein the densifying agent is selected from the group consisting of alkaline earth sulfates, and alkaline earth phosphates.

6. The process according to claim 8, wherein the densifying agent is calcium sulfate or di-calcium phosphate dihydrate.

7. A process for producing a vitamin B-12 composition, comprising the steps of:
    (a) dissolving approximately 1% by weight of vitamin B-12 and approximately 10% by weight of maltodextrin in an aqueous solution;
    (b) suspending approximately 89% by weight of calcium sulfate having a particle size ranging from approximately 40 mesh to approximately 325 mesh in the solution to form a suspension; and
    (c) spray drying the suspension to produce a vitamin B-12 composition, whereby in the composition the vitamin B-12 and the maltodextrin are adhered around individual particles of the calcium sulfate in such a manner that the particle size of the calcium sulfate determines the particle size of the vitamin B-12 composition.

8. A substantially dried micronutrient composition comprising up to approximately 15% by weight of a micronutrient and from approximately 7% to approximately 10% by weight of a binder selected from the group consisting of maltodextrin and gelate, the micronutrient and binder being adhered around individual particles of a densifying agent, the total amount of densifying agent representing from approximately 75% to approximately 92% by weight of the composition, the individual particles of densifying agent having a particle size ranging from approximately 40 mesh to approximately 325 mesh, so that particles of the composition are of a size commensurate with the particle size of the densifying agent, the composition having a tapped density of about 0.7 g/cc to about 1.2 g/cc.

9. The composition according to claim 8, wherein the micronutrient is vitamin B-12.

10. The composition according to claim 8, wherein the micronutrient is folic acid.

11. The composition according to claim 8, wherein the micronutrient is biotin.

12. The composition according to claim 8, wherein the densifying agent is selected from the group consisting of alkaline earth sulfates, and alkaline earth phosphates.

13. The composition according to claim 8, wherein the densifying agent is calcium sulfate or di-calcium phosphate dihydrate.

14. A substantially dried vitamin B-12 composition comprising 1% by weight of vitamin B-12 and approximately 10% by weight of maltodextrin, adhered around individual particles of calcium sulfate which form approximately 89% by weight of the composition and have a particle size ranging from approximately 40 mesh to approximately 325 mesh, so that the particle size of the composition formed is commensurate with the particle size of the densifying agent, the composition having a tapped density of about 0.7 g/cc to about 1.2 g/cc.

* * * * *

UNITED STATES PATENT AND TRADEMARK OFFICE
CERTIFICATE OF CORRECTION

PATENT NO. : 5,397,576
DATED : March 14, 1995
INVENTOR(S) : William Joseph Mergens and Joseph Edward Raymond It is certified that error appears in the above-identified patent and that said Letters Patent is hereby corrected as shown below:

In claim 8, column 6, line 58, delete "gelate" and insert -- gelatin --.

Signed and Sealed this

Sixteenth Day of May, 1995

*Attest:*

BRUCE LEHMAN

*Attesting Officer*     *Commissioner of Patents and Trademarks*